United States Patent
Maruyama et al.

(10) Patent No.: US 10,406,107 B2
(45) Date of Patent: Sep. 10, 2019

(54) METHOD OF PREPARING COMPOSITE GRANULE COMPRISING LOW-SUBSTITUTED HYDROXYPROPYL CELLULOSE AND RAPID RELEASE PREPARATION

(71) Applicant: Shin-Etsu Chemical Co., Ltd., Tokyo (JP)

(72) Inventors: Naosuke Maruyama, Niigata-ken (JP); Yasuyuki Hirama, Nigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/909,516

(22) Filed: Jun. 4, 2013

(65) Prior Publication Data

US 2013/0338238 A1 Dec. 19, 2013

(30) Foreign Application Priority Data

Jun. 15, 2012 (JP) ................................ 2012-135714

(51) Int. Cl.
| | |
|---|---|
| *A61K 9/20* | (2006.01) |
| *A61K 31/167* | (2006.01) |
| *A61K 31/375* | (2006.01) |
| *A61K 9/00* | (2006.01) |
| *A61K 47/38* | (2006.01) |

(52) U.S. Cl.
CPC .......... *A61K 9/2054* (2013.01); *A61K 9/0056* (2013.01); *A61K 9/2095* (2013.01); *A61K 31/167* (2013.01); *A61K 31/375* (2013.01); *A61K 47/38* (2013.01); *A61K 9/2018* (2013.01)

(58) Field of Classification Search
CPC .. A61K 9/2018; A61K 9/2095; A61K 9/1623; A61K 9/2054
See application file for complete search history.

(56) References Cited

U.S. PATENT DOCUMENTS

| | | | |
|---|---|---|---|
| 5,855,914 A | 1/1999 | Koyama et al. | |
| 7,727,548 B2 | 6/2010 | Morita et al. | |
| 8,263,123 B2 | 9/2012 | Morita et al. | |
| 8,303,868 B2 | 11/2012 | Maruyama | |
| 2002/0058714 A1* | 5/2002 | Maruyama | ................. 514/781 |
| 2003/0086967 A1 | 5/2003 | Morita et al. | |
| 2006/0141128 A1* | 6/2006 | Ohkouchi | ........... A61K 31/155 427/2.1 |
| 2008/0014262 A1* | 1/2008 | Morita et al. | ................. 424/464 |
| 2008/0138427 A1* | 6/2008 | Nagahara | ............. A61K 9/1676 424/490 |
| 2010/0187706 A1* | 7/2010 | Maruyama | ........... A61K 9/2018 264/6 |
| 2012/0135991 A1 | 5/2012 | Fujiwara | |

FOREIGN PATENT DOCUMENTS

| | | |
|---|---|---|
| EP | 2 251 012 A1 | 11/2010 |
| JP | 2002/104956 A | 4/2002 |
| JP | 2010-189384 A | 9/2010 |
| WO | WO-01/064190 A1 | 9/2001 |
| WO | WO-2011/019043 A1 | 2/2011 |

OTHER PUBLICATIONS

Mannitol (http://www.everydayhealth.com/drugs/mannitol) accessed Aug. 13, 2014.*
Antony, P.J. et al. "A New Binder for Pharmaceutical Dosage Forms" Drug Development and Industrial Pharmacy, 23(4), 417-418 (1997).*
Extended European Search Report for Application No. 13169048.9; dated Oct. 4, 2013.
Office Action for European Application No. 13169048.9 dated May 28, 2015.
Shimizu et al., *Formulation Study for Lansoprazole Fast-disintegrating Tablet. III. Design of Rapidly Disintegrating Tablets*, Chemical and Pharmaceutical Bulletin, vol. 51, No. 10 (Jan. 2003) 1121-1127.
Office Action for Japanese Application No. 2016-097208 dated Jun. 1, 2017.
Tsuda et al., *Method for Producing Drugs*, Basic Lecture of Development of Pharmaceuticals XI, vol. 1, Jul. 10, 1971, pp. 133-135.

* cited by examiner

*Primary Examiner* — Andrew S Rosenthal
(74) *Attorney, Agent, or Firm* — Alston & Bird LLP

(57) ABSTRACT

Provided is a base material for dry direct tableting, the material being excellent in a binding property and disintegrability. More specifically, provided is a method of preparing a composite granule comprising at least a step of granulating a second sugar or sugar alcohol while adding thereto an aqueous dispersion comprising at least low-substituted hydroxypropyl cellulose having a degree of hydroxypropoxy substitution of 5 to 16% by weight, polyvinyl alcohol, a first sugar or sugar alcohol, and water.

5 Claims, No Drawings

METHOD OF PREPARING COMPOSITE GRANULE COMPRISING LOW-SUBSTITUTED HYDROXYPROPYL CELLULOSE AND RAPID RELEASE PREPARATION

BACKGROUND OF THE INVENTION

1. Field of the Invention

The invention relates to a composite granule comprising low-substituted hydroxypropyl cellulose bringing disintegrability or a binding property in production of the preparation for pharmaceuticals or food; and a rapid release preparation. The invention particularly relates to an orally fast disintegrating tablet excellent in a binding property and disintegrability.

2. Description of the Related Art

In recent years, there has been a demand for the development of orally fast disintegrating tablets which patients inferior in swallowing ability such as the elderly and children can take easily without water. For example, WO01/064190 discloses a method of preparing such tablets by forming a drug, a sugar and a water-soluble polymer such as polyvinyl alcohol into a shape in a wet state and then drying it.

There has also been a demand for the development of a method of preparing orally fast disintegrating tablets without using a special technology or special apparatus. Under such a circumstance, the dry direct tableting method comprising the steps of simply mixing a drug with an additive, adding a lubricant thereto for further mixing, and compressing the resulting mixture into tablets, is a highly productive method having neither a granulation step nor a drying step.

It is described in JP 2002-104956A that a base material for dry direct tableting is obtained by impregnating low-substituted hydroxypropyl cellulose with a sugar or sugar alcohol and then drying the resulting mixture. It is described in WO2011/019043 that an orally fast disintegrating tablet comprises a granule containing a drug, a water-soluble polymer such as polyvinyl alcohol, and a sugar alcohol; and spray-dried particles containing mannitol or mannitol and xylitol as a drug-free tableting base material, carboxymethyl cellulose, and a disintegrant such as low-substituted hydroxypropyl cellulose. A method of granulating a sugar or sugar alcohol while spraying thereto an aqueous dispersion of low-substituted hydroxypropyl cellulose is described in JP 2010-189384A.

SUMMARY OF THE INVENTION

The method described in WO01/064190 requires a special technology and equipment. The dry direct tableting method described in JP 2002-104956A does not comprise a granulation step for improving the flowability of powder so that an additive used in this method should have good flowability to achieve high-speed continuous tableting and the base material should have a sufficient shape-forming property upon dry compression of powder. Thus, a base material for preparing orally fast disintegrating tablets is required to have further improvement in a shape-forming property and disintegrability. In WO2011/019043, the spray dried particles comprising mannitol or mannitol and xylitol, carboxymethyl cellulose, and a disintegrant such as low-substituted hydroxypropyl cellulose are excellent in disintegrability but have insufficient shape-forming property. In addition, since carboxymethyl cellulose is an ionic disintegrant, it sometimes causes interaction with a drug. The granule obtained by the method of JP 2010-189384A is excellent in disintegrability but is desired to have further improvement of the shape-forming property.

With the foregoing in view, the invention has been made. An object of the invention is to provide a base material excellent in a binding property and disintegrability.

The present inventors have carried out an extensive investigation in order to achieve the above-mentioned object. As a result, it has been found that an orally fast disintegrating tablet having high tablet hardness and excellent disintegrability can be obtained by tableting a granule, which has been obtained by making use of a method for preparing a composite granule comprising a step of granulating a sugar or sugar alcohol while using an aqueous dispersion comprising at least low-substituted hydroxypropyl cellulose, polyvinyl alcohol, another sugar or sugar alcohol, and water, leading to the completion of the invention.

According to the invention, there is provided a method for preparing a composite granule comprising at least a step of granulating a second sugar or sugar alcohol while adding thereto an aqueous dispersion comprising at least low-substituted hydroxypropyl cellulose having a degree of hydroxypropoxy substitution of 5 to 16% by weight, polyvinyl alcohol, a first sugar or sugar alcohol, and water. There is also provided a rapid release tablet comprising at least the composite granule prepared in the above-described method and a drug.

According to the invention, a tablet having high tablet hardness and excellent disintegrabililty can be obtained by using the composite granule without using a special method or a special apparatus. The composite granule has excellent disintegrability in the oral cavity and has strength necessary and enough for tablet production or transport so that a tablet facilitating excellent intake can be prepared when a various drug in pharmaceutical or food fields is orally administered. Moreover, according to the invention, since the composite granule is nonionic and has low hygroscopicity, a rapid release preparation excellent in stability can be prepared.

DETAILED DESCRIPTION OF THE PREFERRED EMBODIMENTS

The aqueous dispersion comprising low-substituted hydroxypropyl cellulose, polyvinyl alcohol, and a first sugar or sugar alcohol may be prepared by dissolving the polyvinyl alcohol and the first sugar or sugar alcohol in a predetermined amount of water and then adding the low-substituted hydroxypropyl cellulose into the resulting solution or on the contrary, adding the resulting solution into low-substituted hydroxypropyl cellulose. The low-substituted hydroxypropyl cellulose is water-insoluble, and does not require much time to complete the dispersing operation. The aqueous dispersion can be obtained only by mixing them with a conventional stirrer for a few minutes. During the granulation, the aqueous dispersion is preferably stirred in order to prevent precipitation.

The solid concentration in the aqueous dispersion is preferably from 1 to 30% by weight, more preferably from 10 to 25% by weight. When the solid concentration is less than 1% by weight, the productivity may be lowered because it takes a long time to spray a predetermined amount of the aqueous dispersion. When the solid concentration is more than 30% by weight, the aqueous dispersion may not be fed because the viscosity of the aqueous solution becomes excessively high. The solid concentration in the aqueous dispersion means a concentration of solids which are produced by drying of the aqueous dispersion and will constitute the composite granule.

Low-substituted hydroxypropyl cellulose is a water-insoluble polymer. It absorbs water and swells therewith. It has cellulose as a basic skeleton thereof and a small amount of hydroxypropoxy groups has been introduced therein. The degree of hydroxypropoxy substitution of the low-substituted hydroxypropyl cellulose is from 5 to 16% by weight, preferably from 5 to 9% by weight. When the low-substituted hydroxypropyl cellulose has a degree of hydroxypropoxy substitution of less than 5% by weight, it does not swell sufficiently after water absorption. As a result, the composite granule comprising it sometimes fails to exhibit intended disintegrability or may have a deteriorated binding property. When the low-substituted hydroxypropyl cellulose has a degree of hydroxypropoxy substitution of more than 16% by weight, it has a high swelling property, which leads to improvement in binding property. Owing to increased water solubility, however, the resulting composite granule sometimes fails to exhibit intended disintegrability and the tablets comprising it sometimes needs longer time for disintegration.

The average particle size of the low-substituted hydroxypropyl cellulose is preferably from about 5 to 100 μm, more preferably from about 20 to 60 μm. When the low-substituted hydroxypropyl cellulose has an average particle size of less than 5 μm, a swelling property in water may be lowered and disintegrability may be lowered. When the low-substituted hydroxypropyl cellulose has an average particle size of more than 100 μm, a binding property may be lowered owing to a reduction in the specific surface area. It is noted that the average particle size means a volume-based particle size and is determined by a powder particle size measurement method with laser diffraction. For example, "HELOS & LODOS" (product of Japan Laser) can be used for the measurement.

The low-substituted hydroxypropyl cellulose is used in an amount of preferably from 1 to 15 parts by weight, more preferably from 2 to 10 parts by weight based on 100 parts by weight of the sugar or sugar alcohol in the composite granule. When it is used in an amount of less than 1 parts by weight, a tablet having intended disintegrability may not be obtained. When it is used in an amount of more than 15 parts by weight, the texture in the oral cavity may be deteriorated owing to the increased amount of water-insoluble substance and the stability of the preparation may be lowered owing to the increased hygroscopicity. The amount of the sugar or sugar alcohol in the composite granule means a total amount of the first sugar or sugar alcohol in the aqueous dispersion and the second sugar or sugar alcohol to which the aqueous dispersion is added.

Polyvinyl alcohol is a water-soluble polymer and is used as a binder. The polyvinyl alcohol is prepared by polymerization of a vinyl acetate monomer and the subsequent saponification with an alkali. The polyvinyl alcohol is classified, depending on the degree of saponification, into a partially saponified type having a degree of saponification of from 80 to 90 mol %, an intermediately saponified type having a degree of saponification of more than 90 mol % but less than 98 mol %, and a completely saponified type having a degree of saponification of 98 mol % or more. The partially saponified type polyvinyl alcohol is soluble in normal temperature water, while the completely saponified type polyvinyl alcohol is not soluble in normal temperature water but soluble in hot water of 90° C. or greater. The completely saponified type polyvinyl alcohol has more hydroxyl groups and therefore forms more hydrogen bonds in comparison with the partially saponified type polyvinyl alcohol. Accordingly, the completely saponified type polyvinyl alcohol has the enhanced shape-forming property and is preferable. The intermediately saponified type polyvinyl alcohol has intermediate properties between the partially and completely saponified type polyvinyl alcohols.

A degree of polymerization of the polyvinyl alcohol is preferably from about 500 to 2000. The polyvinyl alcohol having such a degree of polymerization is commercially available. The degree of polymerization and the degree of saponification can be measured according to JIS K6726.

The polyvinyl alcohol is used in an amount of preferably from 0.05 to 0.4 parts by weight, more preferably from 0.1 to 0.3 parts by weight based on 100 parts by weight of the sugar or sugar alcohol in the composite granule. When the polyvinyl alcohol is used in an amount of less than 0.05 parts by weight, the intended shape-forming property may not be attained. When the polyvinyl alcohol is used in an amount of more than 0.4 part by weight, the disintegrability may be lowered although the shape-forming property is excellent.

Examples of the first or second sugar or sugar alcohol include mannitol, trehalose, xylitol, erythritol, lactose and sucrose. The first sugar or sugar alcohol in the aqueous dispersion and the second sugar or sugar alcohol to which the aqueous dispersion is added are not particularly limited and may be the same or different with respect to the kind of sugar or sugar alcohol.

The average particle size of the first sugar or sugar alcohol to be dissolved in the aqueous dispersion is not particularly limited insofar as the first sugar or sugar alcohol can be dissolved therein.

The average particle size of the second sugar or sugar alcohol to which the aqueous dispersion is added is preferably from 5 to 100 μm, more preferably from 10 to 50 μm. When the average particle sizes is less than 5 μm, flowability or disintegrability may be lowered. When the average particle size is more than 100 μm, the shape-forming property may be lowered, or the amount of undissolved portion may increase when the aqueous dispersion is added to the second sugar or sugar alcohol. It is noted that the average particle size of the first or second sugar or sugar alcohol is a volume-based particle size and can be measured using a powder particle size measurement method with laser diffraction. For example, HELOS & RODOS (product of Japan Laser) can be used for the measurement.

The first sugar or sugar alcohol and the second sugar or sugar alcohol are used in the total amount of preferably from 80 to 98% by weight, more preferably from 90 to 95% by weight in the composite granule. When they are used in the total amount of less than 80% by weight, the texture in the oral cavity may be deteriorated, or the stability of the preparation may be lowered owing to an increase of hygroscopicity caused by an increase in the amount of another additive. When it is used in the total amount of more than 98% by weight, the intended binding property or disintegrability may not be attained.

The first sugar or sugar alcohol to be contained by the aqueous dispersion is in an amount of preferably from 1 to 50% by weight, more preferably from 5 to 30% by weight in the total amount of the sugar or sugar alcohol in the composite granule. When it is in an amount of less than 1% by weight, the shape-forming property or the disintegrability may be deteriorated. When it is in an amount of more than 50% by weight, a large amount of undissolved portion may remain, or precipitation or clogging may occur during feeding.

According to the invention, the composite granule is not a simple physical mixture of the sugar or sugar alcohol, the low-substituted hydroxypropyl cellulose and the polyvinyl alcohol, but a particle having the low substituted hydroxypropyl cellulose and the polyvinyl alcohol on the surface of the sugar or sugar alcohol. The sugar or sugar alcohol is soluble in water. The sugar or sugar alcohol is inferior in the shape-forming property by compression so that tableting trouble such as capping is apt to occur. According to the invention, the composite granule is excellent in a binding property and disintegrability because the surface of the sugar or sugar alcohol is covered with low-substituted hydroxypropyl cellulose serving as a disintegrant and polyvinyl alcohol serving as a binder.

According to the invention, examples of an apparatus which can be used for granulation in the invention include a fluidized bed granulator, a stirring granulator, a tumbling fluidized bed granulator, and a spray drying granulator. The fluidized bed granulator is preferable because it can conduct spraying and drying simultaneously and facilitates formation of a uniform covering layer on the powder surface.

The granulation will be described with respect to the fluidized bed granulation as an example. A composite granule can be obtained by charging a powder such as the second sugar or sugar alcohol in a fluid bed and granulating it while spraying thereto an aqueous dispersion as a binder liquid comprising low-substituted hydroxypropyl cellulose, polyvinyl alcohol, and the first sugar or sugar alcohol.

Although the average particle size of the composite granule differs depending on the granulation conditions, it is preferably from 50 to 300 µm. When the average particle size is less than 50 µm, the flowability is low so that sticking of the granule to a tableting machine may be caused. When the average particle size is more than 300 µm, uniformity of filling of the granule in a mortar may be lowered and may cause a larger weight deviation in a tablet. The average particle size of the granule can be measured using the sieving method described in the General Tests of the Japanese Pharmacopoeia.

When the composite granule is obtained by drying with a fluidized bed granulator capable of simultaneously spraying and drying, further drying is not necessary. When the fluidized bed granulator is used without drying, or a granulator incapable of drying is used, the drying can be carried out in a known manner such as drying at 40 to 80° C. by using a fluidized bed dryer or a shelf dryer. The water content of the composite granule thus obtained is preferably 5% by weight or less, more preferably 1% by weight or less. Water the water content is more than 5% by weight, the stability of the preparation may be adversely affected.

According to the invention, a rapid release tablet comprising at least the composite granule thus obtained and a drug can be provided.

The production of a tablet comprising the composite granule through a dry direct tableting method will be explained. The composite granule and a drug are mixed, then a small amount of a lubricant is added thereto and mixed, and subjected to compression into tablets at a predetermined pressure by using a conventional rotary continuous tableting machine. The size of the tablet can be selected freely. The tablet preferably has a diameter of from about 6 to 12 mm and a weight of from 70 to 700 mg/tablet. When the tablet has a diameter of less than 6 mm, it may not be handled easily. When the tablet has a diameter of more than 12 mm, it may be hard to swallow.

The tableting pressure during tableting is preferably from 10 to 300 MPa. When the tableting pressure is less than 10 MPa, intended tablet hardness may not be obtained. When the tableting pressures is more than 300 MPa, tableting trouble such as capping may be caused.

According to the invention, the drug usable in the tablet comprising the composite granule is not particularly limited. Examples of the drug include a drug for central nervous system, a drug for circulatory system, a drug for respiratory system, a drug for digestive system, antibiotics and chemotherapeutic agents, a drug for metabolic system, and a vitamin drug.

Examples of the drug for central nervous system include diazepam, idebenone, aspirin, ibuprofen, paracetamol, naproxen, piroxicam, diclofenac, indomethacin, sulindac, lorazepam, nitrazepam, phenytoin, acetaminophen, ethenzamide and ketoprofen.

Examples of the drug for circulatory system include molsidomine, vinpocetine, propranolol, methyldopa, dipyridamole, furosemide, triamterene, nifedipine, atenolol, spironolactone, metoprolol, pindolol, captopril and isosorbide nitrate.

Examples of the drug for respiratory system include amlexanox, dextromethorphan, theophylline, pseudoephedrine, salbutamol and guaifenesin.

Examples of the drug for digestive system include benzimidazole-based drug having antiulcer activity such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole, cimetidine, ranitidine, pancreatin, bisacodyl and 5-aminosalicylic acid.

Examples of the antibiotics and chemotherapeutic agents include cephalexin, cefaclor, cefradine, amoxicillin, pivampicillin, bacampicillin, dicloxacillin, erythromycin, erythromycin stearate, lincomycin, doxycycline and trimethoprim/sulfamethoxazole.

Examples of the drug for metabolic system include serrapeptase, lysozyme chloride, adenosine triphosphate, glibenclamide and potassium chloride.

Examples of the vitamin drug include vitamin $B_1$, vitamin $B_2$, vitamin $B_6$ and vitamin C.

In the production of tablets, an additive other than the composite granule and commonly used for a solid preparation may be added in a commonly used amount. Examples of such an additive include a disintegrant, a binder, an extender, a lubricant, a taste corrigent and a flavor.

Examples of the disintegrant include low-substituted hydroxypropyl cellulose, corn starch, potato starch, partly pregelatinized starch, carboxymethyl starch sodium, carmellose, croscarmellose sodium, crystalline cellulose and crospovidone. Examples of the binder include hydroxypropyl cellulose, polyvinylpyrrolidone and hydroxypropylmethyl cellulose.

Examples of the extender include erythritol, mannitol, sorbitol, lactose, sucrose, calcium phosphate and calcium sulfate.

Examples of the taste corrigent include citric acid, tartaric acid and malic acid.

Examples of the flavor include menthol, peppermint oil and vanillin.

Examples of the lubricant include magnesium stearate and sucrose fatty acid ester.

According to the invention, an aqueous dispersion comprising at least low-substituted hydroxypropyl cellulose, polyvinyl alcohol, and a first sugar or sugar alcohol is added (preferably sprayed) to coat a surface of a second sugar or sugar alcohol to modify the surface. Consequently, both the enhanced shape-forming property and fast disintegrability can be obtained. The reason why both the enhanced shape-forming property and the fast disintegrability can be obtained is considered to be that the surface of the composite granule is covered with the low-substituted hydroxypropyl cellulose and the polyvinyl alcohol, where the low-substituted hydroxypropyl cellulose and the polyvinyl alcohol having many hydroxyl groups contribute to formation of firm hydrogen bonds at the time of compression molding, leading to improvement of a binding property. It is also considered to be that the low-substituted hydroxypropyl cellulose has a property of quickly absorbing water and swelling therewith so that the compression molded product thus obtained disintegrates rapidly.

EXAMPLES

The invention will hereinafter be described specifically by Examples and Comparative Examples. It should not be construed that the invention is limited to or by the following Examples.

Example 1

To 316 g of purified water were added 8 g of an aqueous 10% by weight solution of polyvinyl alcohol having a degree of saponification of 98.5 mol % and a degree of polymerization of 1700 and 60 g of D-mannitol. The resulting mixture was agitated with an agitating blade to obtain an aqueous solution. Next, 16 g of low-substituted hydroxypropyl cellulose having a degree of hydroxypropoxy substitution of 8% by weight was added to the obtained aqueous solution and mixed to prepare an aqueous dispersion. Then, 323.2 g of D-mannitol was placed in a fluidized bed granulator, and granulation was carried out while spraying thereto the aqueous dispersion at an intake gas temperature of 60° C., an exhaust gas temperature of 25 to 28° C., an air flow of 50 m$^3$/hr, a spray rate of 12 g/min, and a spray air pressure of 150 kPa. The composition of the aqueous dispersion and the powder to be granulated are shown in Table 1.

After 0.5 part by weight of magnesium stearate as a lubricant was added to 100 parts by weight of the obtained composite granule and mixed, the resulting mixture was tableted into tablets by using a rotary tableting machine at a tableting pressure of 7.5 kN. Each tablet had a diameter of 8 mm, a curvature radius of 12 mm, and a weight of 200 mg. The tablet hardness, disintegration time of the Japanese Pharmacopoeia, and oral disintegration time of the tablet were measured. The results and the composition of the composite granule are shown in Table 2. The tablet hardness was a measurement value of the maximum breaking strength at which the tablet was broken as a result of application of a load at a rate of 1 mm/sec in a diameter direction of the tablet. The disintegration time of the Japanese Pharmacopoeia was measured using water as a test liquid in accordance with the disintegration test of the Japanese Pharmacopoeia. The oral disintegration time without a disk was obtained by placing a tablet on the tongue of each of six healthy adults, measuring time required for each tablet to disintegrate in the oral cavity, and averaging the time.

Example 2

To 324 g of purified water were added 8 g of an aqueous 10% by weight solution of polyvinyl alcohol having a degree of saponification of 98.5 mol % and a degree of polymerization of 1700 and 60 g of D-mannitol. The resulting mixture was agitated with an agitation blade to obtain an aqueous solution. Next, 8 g of low-substituted hydroxypropyl cellulose having a degree of hydroxypropoxy substitution of 8% by weight was added to the obtained aqueous solution and mixed to prepare an aqueous dispersion. Then, 331.2 g of D-mannitol was placed in a fluidized bed granulator, and granulation was carried out while spraying thereto the aqueous dispersion at an intake gas temperature of 60° C., an exhaust gas temperature of 25 to 28° C., an air flow of 50 m$^3$/hr, a spray rate of 12 g/min, and a spray air pressure of 150 kPa. The composition of the aqueous dispersion and the powder to be granulated are shown in Table 1.

The composite granule thus obtained was tableted in the same manner as in Example 1 and the tablets thus obtained were evaluated also in the same manner. The results are shown in Table 2.

Example 3

To 528 g of purified water were added 8 g of an aqueous 10% by weight solution of polyvinyl alcohol having a degree of saponification of 98.5 mol % and a degree of polymerization of 1700 and 60 g of D-mannitol. The resulting mixture was agitated with an agitation blade to obtain an aqueous solution. Next, 40 g of low-substituted hydroxypropyl cellulose having a degree of hydroxypropoxy substitution of 8% by weight was added to the obtained aqueous solution and mixed to prepare an aqueous dispersion. Then, 299.2 g of D-mannitol was placed in a fluidized bed granulator, and granulation was carried out while spraying thereto the aqueous dispersion at an intake gas temperature of 60° C., an exhaust gas temperature of 25 to 28° C., an air flow of 50 m$^3$/hr, a spray rate of 12 g/min, and a spray air pressure of 150 kPa. The composition of the aqueous dispersion and the powder to be granulated are shown in Table 1.

The composite granule thus obtained was tableted in the same manner as in Example 1 and the tablets thus obtained were evaluated also in the same manner. The results are shown in Table 2.

Example 4

To 312 g of purified water were added 4 g of an aqueous 10% by weight solution of polyvinyl alcohol having a degree of saponification of 88 mol % and a degree of polymerization of 500 and 40 g of erythritol. The resulting mixture was agitated with an agitation blade to obtain an aqueous solution. Next, 24 g of low-substituted hydroxypropyl cellulose having a degree of hydroxypropoxy substitution of 11% by weight was added to the obtained aqueous solution and mixed to prepare an aqueous dispersion. Then, 315.6 g of erythritol was placed in a fluidized bed granulator, and granulation was carried out while spraying thereto the aqueous dispersion at an intake gas temperature of 60° C., an exhaust gas temperature of 25 to 28° C., an air flow of 50 m$^3$/hr, a spray rate of 12 g/min, and a spray air pressure of 150 kPa. The composition of the aqueous dispersion and the powder to be granulated are shown in Table 1.

The composite granule thus obtained was tableted in the same manner as in Example 1 and the tablets thus obtained were evaluated also in the same manner. The results are shown in Table 2.

Example 5

To 304 g of purified water were added 12 g of an aqueous 10% by weight solution of polyvinyl alcohol having a degree of saponification of 88 mol % and a degree of polymerization of 1700 and 60 g of erythritol. The resulting mixture was agitated with an agitation blade to obtain an aqueous solution. Next, 24 g of low-substituted hydroxypropyl cellulose having a degree of hydroxypropoxy substitution of 11% by weight was added to the obtained aqueous solution and mixed to prepare an aqueous dispersion. Then, 314.8 g of lactose was placed in a fluidized bed granulator, and granulation was carried out while spraying thereto the aqueous dispersion at an intake gas temperature of 60° C., an exhaust gas temperature of 25 to 28° C., an air flow of 50 m³/hr, a spray rate of 12 g/min, and a spray air pressure of 150 kPa. The composition of the aqueous dispersion and the powder to be granulated are shown in Table 1.

The composite granule thus obtained was tableted in the same manner as in Example 1 and the tablets thus obtained were evaluated also in the same manner. The results are shown in Table 2.

Comparative Example 1

A powder mixture having the same composition as that in Example 2 and obtained by physically mixing the powders shown below was tableted without granulation.

The 391.2 g of D-mannitol, 8 g of low-substituted hydroxypropyl cellulose having a degree of hydroxypropoxy substitution of 8% by weight, and 0.8 g of polyvinyl alcohol having a degree of saponification of 98.5 mol % and a degree of polymerization of 1700 were mixed. The 0.5 part by weight of magnesium stearate as a lubricant was added thereto based on 100 parts by weight of the powder mixture thus obtained, and mixed. The resulting mixture was tableted using a rotary tableting machine under the same conditions as those in Example 1. The tablets thus obtained were evaluated for tablet hardness, disintegration time of the Japanese Pharmacopoeia, and oral disintegration time. The results are shown in Table 2.

Comparative Example 2

Granulation was carried out using an aqueous dispersion of low-substituted hydroxypropyl cellulose in accordance with the method described in JP 2010-189384A.

To 316 g of purified water was added 16 g of low-substituted hydroxypropyl cellulose having a degree of hydroxypropoxy substitution of 8% by weight, and mixed to prepare an aqueous dispersion. Next, 384 g of D-mannitol was placed in a fluidized bed granulator, and granulation was carried out while spraying thereto the aqueous dispersion at an intake gas temperature of 60° C., an exhaust gas temperature of 25 to 28° C., an air flow of 50 m³/hr; a spray rate of 12 g/min, and a spray air pressure of 150 kPa. The composition of the aqueous dispersion and the powder to be granulated are shown in Table 1.

The composite granule thus obtained was tableted in the same manner as in Example 1 and the tablets thus obtained were evaluated also in the same manner. The results are shown in Table 2.

Comparative Example 3

Under the same conditions as those in Example 1 except for the use of croscarmellose sodium instead of the low-substituted hydroxypropyl cellulose in Example 1, granulation was carried out. The composition of the aqueous dispersion and the powder to be granulated are shown in Table 1.

The granule thus obtained was tableted in the same manner as in Example 1. The tablets thus obtained were evaluated also in the same manner. The results are shown in Table 2.

Comparative Example 4

Under the same conditions as those in Example 1 except for the use of hydroxypropyl cellulose having a degree of hydroxypropoxy substitution of 64% by weight instead of the polyvinyl alcohol in Example 1, granulation was carried out. The composition of the aqueous dispersion and the powder to be granulated are shown in Table 1.

The granule thus obtained was tableted in the same manner as in Example 1 and the tablets thus obtained were evaluated also in the same manner. The results are shown in Table 2.

TABLE 1

|  | composition of aqueous dispersion (part by weight) | | | | | | | | powder to be granulated (part by weight) | | | | |
|---|---|---|---|---|---|---|---|---|---|---|---|---|---|
|  |  |  | sugar or sugar alcohol | | | | | |  |  | sugar or sugar alcohol | | |
|  | L-HPC | PVA | mannitol | erythritol | lactose | cl-CMC-Na | HPC | purified water | L-HPC | PVA | mannitol | erythritol | lactose |
| Example 1 | 4.0 | 0.2 | 15.0 | — | — | — | — | 80.8 | — | — | 80.8 | — | — |
| Example 2 | 2.0 | 0.2 | 15.0 | — | — | — | — | 82.8 | — | — | 82.8 | — | — |
| Example 3 | 10.0 | 0.2 | 15.0 | — | — | — | — | 74.8 | — | — | 74.8 | — | — |
| Example 4 | 6.0 | 0.1 | — | 15.0 | — | — | — | 78.9 | — | — | — | 78.9 | — |
| Example 5 | 6.0 | 0.3 | — | 15.0 | — | — | — | 78.7 | — | — | — | — | 78.7 |
| Comp.Ex.1 | — | — | — | — | — | — | — | — | 2.0 | 0.2 | 97.8 | — | — |
| Comp.Ex.2 | 4.0 | — | — | — | — | — | — | 96.0 | — | — | 96.0 | — | — |
| Comp.Ex.3 | — | 0.2 | 15.0 | — | — | 4.0 | — | 80.8 | — | — | 80.8 | — | — |
| Comp.Ex.4 | 4.0 | — | 15.0 | — | — | — | 0.2 | 80.8 | — | — | 80.8 | — | — |

"L-HPC" represents low-substituted hydroxypropyl cellulose, while "PVA" represents polyvinyl alcohol.
"cl-CMC-Na" represents croscarmellows sodium, while "HPC" represents hydroxypropyl cellulose.

TABLE 2

| | composition of composite granule (part by weight) | | | | | | | | | tablet properties | | |
|---|---|---|---|---|---|---|---|---|---|---|---|---|
| | | | sugar or sugar alcohol | | | | | blend ratio | blend ratio | hardness | disintegration time of Japan Pharmacopoeia | oral disintegration time |
| | L-HPC | PVA | mannitol | erythritol | lactose | cl-CMC-Na | HPC | A | B | (N) | (second) | (second) |
| Example 1 | 4.0 | 0.2 | 95.8 | — | — | — | — | 0.042 | 0.0021 | 93.0 | 14.6 | 15.7 |
| Example 2 | 2.0 | 0.2 | 97.8 | — | — | — | — | 0.020 | 0.0020 | 87.2 | 17.4 | 20.7 |
| Example 3 | 10.0 | 0.2 | 89.8 | — | — | — | — | 0.111 | 0.0022 | 93.9 | 15.8 | 15.1 |
| Example 4 | 6.0 | 0.1 | — | 93.9 | — | — | — | 0.064 | 0.0011 | 95.1 | 18.1 | 19.1 |
| Example 5 | 6.0 | 0.3 | — | 15.0 | 78.7 | — | — | 0.064 | 0.0032 | 80.8 | 21.2 | 22.5 |
| Comp.Ex.1 | 2.0 | 0.2 | 97.8 | — | — | — | — | 0.020 | 0.0020 | 19.0 | 71.5 | 85.2 |
| Comp.Ex.2 | 4.0 | — | 96.0 | — | — | — | — | 0.042 | — | 38.4 | 14.0 | 15.5 |
| Comp.Ex.3 | — | 0.2 | 95.8 | — | — | 4.0 | — | — | 0.0021 | 80.4 | 40.2 | 60.5 |
| Comp.Ex.4 | 4.0 | — | 95.8 | — | — | — | 0.2 | 0.042 | — | 51.8 | 24.2 | 35.5 |

"L-HPC" represents low-substituted hydroxypropyl cellulsoe, while PVA represents polyvinyl alcohol.
"cl-CMC-Na" represents croscarmellose sodium, while "HPC" represents hydroxypropyl cellulose.
"blend ratio A" represents a weight ratio of L-HPC to sugar or sugar alcohol.
"blend ratio B" represents a weight ratio of PVA to sugar or sugar alcohol.

In Comparative Example 1 in which a simple physical mixture was used, capping occurred during tableting and the tablets having high tablet hardness were not obtained. In addition, their disintegration time was long. The composite granule in Example 2 having the same composition as that in Comparative Example 1 was obtained by granulating a second sugar or sugar alcohol while using an aqueous dispersion comprising low-substituted hydroxypropyl cellulose, polyvinyl alcohol, a first sugar or sugar alcohol and water, and exhibited excellence in the shape-forming property by compression and the disintegrability. It is considered that many hydrogen bonds are formed as a result of coating the surface of the sugar or sugar alcohol having a low shape-forming property with the low-substituted hydroxypropyl cellulose and the polyvinyl alcohol having many hydroxyl groups, and thereby the binding property is enhanced. It is also considered that since the low-substituted hydroxypropyl cellulose rapidly swells with water absorbed therein, tablets comprising the composite granule of the invention show fast disintegration.

In Comparative Example 2 in which granulation was carried out using an aqueous dispersion of low-substituted hydroxypropyl cellulose, the disintegrability was excellent but the shape-forming property was insufficient. In Comparative Example 3 in which croscarmellose sodium as a disintegrant was used instead of the low-substituted hydroxypropyl cellulose, disintegrability was insufficient. In Comparative Example 4 in which water-soluble hydroxypropyl cellulose was used instead of polyvinyl alcohol, both a tablet-forming property and disintegrability were insufficient.

Example 6

The 10 parts by weight of acetaminophen was mixed with 90 parts by weight of the composite granule obtained in Example 1. Then, 0.5 part by weight of magnesium stearate was added thereto as a lubricant and mixed. The resulting mixture was tableted using a rotary tableting machine at a tableting pressure of 5 kN to obtain tablets, each having a diameter of 8 mm, a curvature radius of 12 mm and a weight of 200 mg.

The tablets thus obtained were evaluated for tablet hardness, disintegration time of the Japanese Pharmacopoeia, and oral disintegration time. The results are shown in Table 3.

Example 7

The 10 parts by weight of ascorbic acid was mixed with 90 parts by weight of the composite granule obtained in Example 1. Then, 0.5 part by weight of magnesium stearate was added as a lubricant thereto and mixed. The resulting mixture was tableted using a rotary tableting machine at a tableting pressure of 5 kN to obtain tablets, each having a diameter of 8 mm, a curvature radius of 12 mm, and a weight of 200 mg.

The tablets thus obtained were evaluated for tablet hardness, disintegration time of the Japanese Pharmacopoeia, and oral disintegration time. The results are shown in Table 3.

TABLE 3

| | composition of tablet (part by weight) | | | | tablet properties | | |
|---|---|---|---|---|---|---|---|
| | | | | | | disintegration time of Japan | oral disintegration |
| | composite granule in Example 1 | acetaminophen | ascorbic acid | magnesium stearate | hardness (N) | Pharmacopoeia (second) | time (second) |
| Example 6 | 90.0 | 10.0 | — | 0.5 | 54.1 | 13.1 | 13.5 |
| Example 7 | 90.0 | — | 10.0 | 0.5 | 53.1 | 20.6 | 21.1 |

According to the invention, rapid release tablets were obtained by tableting a mixture of the composite granule and the drug. The tablets thus obtained exhibited excellent oral disintegrability and also excellent texture in the oral cavity.

The invention claimed is:

1. A method of preparing a composite granule for tableting, comprising at least a step of granulating a second sugar or sugar alcohol while spraying thereto an aqueous dispersion comprising at least low-substituted hydroxypropyl cellulose having a degree of hydroxypropoxy substitution of 5 to 16% by weight, polyvinyl alcohol, a first sugar or sugar alcohol, and water, wherein the aqueous dispersion coats a surface of the second sugar or sugar alcohol for surface-modification of the second sugar or sugar alcohol with the low-substituted hydroxypropyl cellulose and the polyvinyl alcohol, and wherein the composite granule is characterized by the absence of a drug except for the first sugar or sugar alcohol and the second sugar or sugar alcohol.

2. The method of preparing a composite granule according to claim 1, wherein the first sugar or sugar alcohol and the second sugar or sugar alcohol may be the same or different and are each at least one selected from the group consisting of mannitol, trehalose, xylitol, erythritol, lactose and sucrose.

3. The method of preparing a composite granule according to claim 1, wherein the low-substituted hydroxypropyl cellulose is comprised in an amount of 1 to 15 parts by weight based on 100 parts by weight of a total amount of the first sugar or sugar alcohol and the second sugar or sugar alcohol.

4. The method of preparing a composite granule according to claim 1, wherein the polyvinyl alcohol is comprised in an amount of 0.05 to 0.4 parts by weight based on 100 parts by weight of a total amount of the first sugar or sugar alcohol and the second sugar or sugar alcohol.

5. A rapid release tablet comprising at least the composite granule prepared by the method as claimed in claim 1 and a drug, and being obtained by mixing the composite granule with the drug.

* * * * *